United States Patent
Savage

(10) Patent No.: US 7,573,182 B2
(45) Date of Patent: Aug. 11, 2009

(54) ULTRASONIC TRANSDUCER

(75) Inventor: James D. Savage, Port Jefferson Station, NY (US)

(73) Assignee: ProRhythm, Inc., Ronkonkoma, NY (US)

( * ) Notice: Subject to any disclaimer, the term of this patent is extended or adjusted under 35 U.S.C. 154(b) by 434 days.

(21) Appl. No.: 11/440,953

(22) Filed: May 25, 2006

(65) Prior Publication Data

US 2006/0273695 A1 Dec. 7, 2006

Related U.S. Application Data

(60) Provisional application No. 60/686,291, filed on Jun. 1, 2005.

(51) Int. Cl.
*H01L 41/08* (2006.01)
(52) U.S. Cl. .................... 310/334; 600/459
(58) Field of Classification Search .............. 310/334; 600/457, 459
See application file for complete search history.

(56) References Cited

U.S. PATENT DOCUMENTS

| | | | |
|---|---|---|---|
| 5,648,941 A * | 7/1997 | King ..................... 367/176 |
| 6,106,474 A | 8/2000 | Koger et al. | |
| 6,128,522 A | 10/2000 | Acker et al. | |
| 6,599,288 B2 | 7/2003 | Maguire et al. | |
| 6,607,502 B1 | 8/2003 | Maguire et al. | |
| 6,763,722 B2 | 7/2004 | Fjield et al. | |
| 6,806,623 B2 * | 10/2004 | Petersen et al. ............. 310/334 |
| 6,891,311 B2 * | 5/2005 | Phelps et al. ................ 310/317 |
| 7,285,266 B2 * | 10/2007 | Vournakis et al. ......... 424/93.72 |
| 2002/0151825 A1 * | 10/2002 | Rubenchik et al. ............. 601/2 |
| 2004/0237970 A1 * | 12/2004 | Vournakis et al. ........... 128/898 |
| 2006/0273695 A1 * | 12/2006 | Savage ...................... 310/341 |

FOREIGN PATENT DOCUMENTS

EP 0 640 564 A1 8/1994

* cited by examiner

*Primary Examiner*—Jaydi SanMartin
(74) *Attorney, Agent, or Firm*—Lerner, David, Littenberg, Krumholz & Mentlik, LLP

(57) ABSTRACT

An ultrasonic transducer of the type containing a cylindrical piezoelectric active element mounted on a supporting tube is provided with a backing component made of an electrically and thermally insulating material forming a sleeve which extends between the piezoelectric element and the supporting tube. An insulating material is selected for the backing component which includes a substantial amount of entrained air. Preferably, the backing component is made of expanded polytetrafluoroethylene (EPTFE).

22 Claims, 2 Drawing Sheets

ULTRASONIC TRANSDUCER

CROSS-REFERENCE TO RELATED APPLICATIONS

This application claims the benefit of the filing date of U.S. Provisional Patent Application No. 60/686,291 filed Jun. 1, 2005, the disclosure of which is hereby incorporated herein by reference.

BACKGROUND OF THE INVENTION

The present invention relates to ultrasonic transducers.

Ultrasonic transducers find wide application in industry and in medicine. For example, in certain medical procedures, they are used to produce ultrasonic energy which heats tissue within the body of a living subject. In one such type of procedure, known as ablation, sufficient heat is applied to kill undesired tissue. Typically, this requires heating tissue to a temperature of 60-80° C. Furthermore, it is desirable that tissue be heated rapidly in order to avoid incidental damage to surrounding tissue.

In one common medical application, ultrasonic transducers are utilized in catheters which must pass through small spaces within the body. For example, catheters are often passed through the circulatory system in order to be placed into the heart. It will be appreciated that the ultrasonic transducers on such catheters must be quite small, yet they must be capable of emitting a substantial amount of ultrasonic power in order to be useful.

A typical ultrasonic transducer utilized in a catheter includes an active element in the form of a piezoelectric sleeve. Piezoelectric elements deform physically when subjected to an electric field. Hence, when a sufficiently rapidly varying electrical signal is applied, the piezoelectric sleeve vibrates at ultrasonic frequencies, and ultrasonic energy is radiated. Typically, the piezoelectric sleeve is mounted on a supporting tube, typically made of surgical steel, which provides a lumen for the catheter. The supporting tube must be electrically isolated from the piezoelectric sleeve. When the piezoelectric sleeve vibrates, it produces substantial heat, and excessive heat must not be transmitted to the supporting tube.

In order to provide efficient ultrasonic radiation, a backing medium is usually provided at the inner face of the piezoelectric sleeve. This backing is made of a material which has a substantially different ultrasonic impedance than the piezoelectric material, so that ultrasonic energy impinging upon the interface between the piezoelectric sleeve and the backing medium is reflected outwardly, increasing the total ultrasonic radiation away from the sleeve.

One known backing medium is air. Air backing is achieved by constructing the transducer so that air is in contact with substantially entire inner surface of the active element, providing the necessary reflection of ultrasonic energy. U.S. Pat. Nos. 6,599,288 and 6,607,502, both to Maguire et al., disclose a catheter wherein the ultrasound transducer is mounted onto a catheter shaft without any support structure between the two, i.e., the transducer is suspended about the catheter shaft. This may isolate the transducer from the shaft by providing a layer of air between the two, however, a catheter with such complicated structure is difficult to manufacture and assemble.

Ultrasonic transducers have also been provided with solid backing. For example, the backing could be a brass sleeve inwardly of the piezoelectric sleeve. FIG. 1 is a schematic representation of the internal construction of a known water backed transducer 10. An active element 12 of transducer 10 is a cylindrical sleeve made of a piezoelectric material. Cables 13 provide an electrical actuating signal for transducer 10. For this purpose, conductive regions (not shown) are provided on the outer and inner surfaces of sleeve 12. One conductor of each of cables 13 is connected to the conductive region on the outer surface of sleeve 12, and the other conductor is connected to a backing element 14. Since backing element 14 is made of an electrically conductive material (see below), it will make the necessary electrical contact with the conductive region on the inner surface of sleeve 12.

Backing element 14 is generally cylindrical, made of brass, and is provided inside piezoelectric sleeve 12. Backing element 14, at each axial end, includes a plurality of radially extending protrusions 14a. The diameter of the rear surface of sleeve 12 is greater than the diameter of the opposed surface of backing element 14, so that a cylindrical space 16 is formed there between. Space 16 is filled with water and absorbs heat generated by active element 12. Backing element 14 has an axial bore which receives a supporting tube 18, made of stainless steel. Between tube 18 and backing element 14, there is provided a layer 20 of polyimide insulation. The water in this water backed transducer 10 provides a coolant which reduces heat transmission to the tube. The water back of transducer 10 therefore serves dual functions of providing ultrasonic reflection and limiting heat transfer to supporting tube 18.

Unfortunately, an ultrasonic transducer with a water back tends to produce ultrasonic energy inefficiently and permits an undesirable amount of heat to buildup in the interior of the transducer. Additionally, due to the small size of the catheter, it is difficult to provide high enough flow rate of water to obtain sufficient cooling effect. Typically, this type of transducer will convert electrical energy to ultrasound energy with an efficiency of about 45%, and the interior (center) of the transducer can be heated to a temperature in excess of 300° F. Moreover, a catheter with this complex structure is difficult to manufacture and assemble.

SUMMARY OF THE INVENTION

The present invention overcomes the shortcomings of the prior art and discloses an ultrasonic transducer having an active element, a backing element, and a support. The backing element is located between and is in contact with the active element and the support. The backing element is hydrophobic, made of an insulating material which contains entrained air and is of sufficient thickness to provide substantial thermal insulation with respect to the active element.

In another aspect the present invention discloses an ultrasonic transducer of the type including a hollow cylindrical active element made of a piezoelectric material and having inner and outer surfaces. The ultrasonic transducer also includes a backing element that is in contact with the inner surface and is mounted on a cylindrical support. The backing element is made of an insulating material which contains entrained air and is hydrophobic.

Another aspect of the present invention discloses an ultrasonic transducer containing an active element having a front and a rear surface, a backing element in contact with the rear surface, and a support, the support being in contact with the backing element. The backing element is made of a soft hydrophobic material that does not significantly dampen the vibrations of the active element. The backing element may be made from a material which includes a substantial amount of entrained air. Preferably, the backing component is made of expanded polytetrafluoroethylene (EPTFE).

BRIEF DESCRIPTION OF THE DRAWINGS

The foregoing brief description and further objects, features and advantages of the present invention will be understood more completely from the following detailed description of a presently preferred, but nonetheless illustrative, embodiment in accordance with the present invention, with the reference being had to the accompanying drawings, in which.

DETAILED DESCRIPTION OF THE PREFERRED EMBODIMENT

Figure 1:
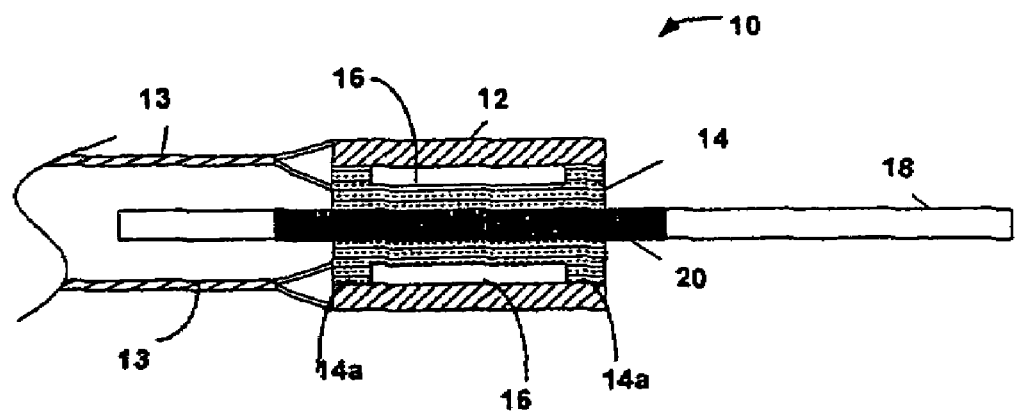
FIG. 1 is a schematic representation of the internal construction of a known water backed transducer shown in lengthwise cross-section.
Figure 2:
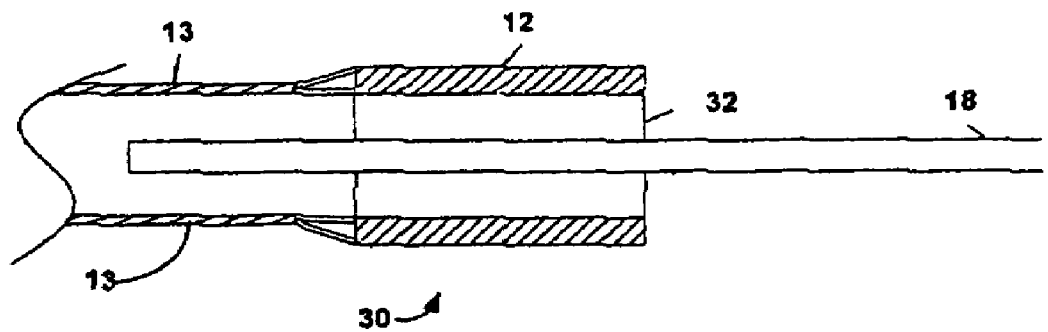
FIG. 2 is a schematic representation of the internal construction of an EPTFE backed transducer, also shown in lengthwise cross-section.

FIG. 2 is a schematic representation of the internal construction of an ultrasonic transducer 30. In this figure, elements which are indicated by the same reference numbers as in FIG. 1 are identical to the corresponding elements of FIG. 1. In FIG. 2, backing element 14 and the insulation layer 20 of FIG. 1 are replaced by a cylindrical sleeve 32 (i.e., backing element) which is made of in insulating material, preferably EPTFE, which fills the entire space between the interior surface of element 14 and the opposed surface of tube 18. EPTFE was selected because it contains entrained air, is hydrophobic and is widely accepted for medical applications inside a living body. However, it is contemplated other materials including other materials containing entrained air may be utilized, so long as they would not be harmful if placed inside a living body and would not deteriorate in that environment. The elimination of water backing element 14 and insulation layer 20 results in simpler construction and easier manufacture and assembly of transducer 30. PTFE is a material which has long been available from DuPont under the trademark TEFLON® (i.e., polytetrafluoroethylene or PTFE). With an EPTFE backing in place of a water backing, the power efficiency of the transducer can be improved by about 20% or more, and the internal temperature of the transducer can be reduced from the range of 310° F. to the range of 220° F.

Since EPTFE sleeve 32 is electrically nonconductive, the electrical conductors of cables 13 which were previously attached to backing element 14 are now connected directly to a conductive area on the inner surface of sleeve 12. Also, the insulation layer 20 of FIG. 1 may be eliminated for the same reason. Otherwise, the structure of transducer 30 is identical to that of transducer 10.

EXAMPLE

Two identical water backed transducers were utilized to test the efficacy of the present transducer construction. One transducer was left unchanged, and on the other, the backing element 14 and insulating layer 20 removed and replaced by sleeve 32 of EPTFE which completely filled the space between transducer 12 and tube 18. EPTFE sleeve 32 was press fitted onto tube 18 and within sleeve 12.

Each transducer was mounted within a brass reflector, placed in a water bath and sonicated at 100 Watts for 60 seconds. During sonication, the power output of the transducer was measured, and at the conclusion of the test, the temperature inside the transducer was measured by a temperature sensor placed within tube 18. The test was repeated several times for reach transducer.

The average power output for the water backed transducer was 45.4 Watts, while the average power output for the EPTFE backed transducer was 54.7 Watts. At the same time, the maximum temperature recorded inside the water backed transducer was 307° F., while the maximum temperature recorded inside the EPTFE backed transducer was 219° F.

There are believed to be a number of reasons for the superior performance of the EPTFE backed transducer. Consideration of these will serve as an effective guide to the selection of alternate insulating materials for the backing element. First of all, the interface between the piezoelectric material of sleeve 12 and EPTFE sleeve (with its entrained air) 32 provides a very effective reflection of ultrasonic energy. However, there is another contribution to the more efficient energy conversion of the EPTFE backed transducer. In the water backed transducer, protrusions 14a effectively damped vibration of sleeve 12 wherever they touch it. EPTFE sleeve 32, on the other hand, is very soft and has no similar deleterious effect on the vibration of sleeve 12. This accounts, in some part, for the more efficient energy conversion of the EPTFE backed transducer.

As far as the reduction in core temperature of the transducer is concerned, this is probably accounted for by the presence of the relatively thick sleeve 32 of insulating material. Additional benefits of the EPTFE backed transducer include the replacement of sleeve 20 and backing element 14 with a much simpler construction involving only a sleeve of insulating material, and the elimination of the complications introduced by the use of water inside the transducer.

In a typical application, tube 18 typically has an outside diameter of approximately 1.14 mm. Transducer 12 might have outside diameter of approximately 1.5-2.5 mm, a wall thickness of approximately 0.1-0.5 mm and a length of approximately 0.5-16 mm. Sleeve 32 would fill the gap between the inside of transducer 12 and tube 18. Sleeve 32 has a wall thickness in the range of approximately 0.25-1.25 mm. Most preferably, transducer 12 is 6 mm in length, has an outside diameter of 2.44 mm and a wall thickness of 0.116 mm. Transducer 12 may have any outside diameter which is appropriate for its application, with a progressively larger thickness for larger transducers.

Figure 3:
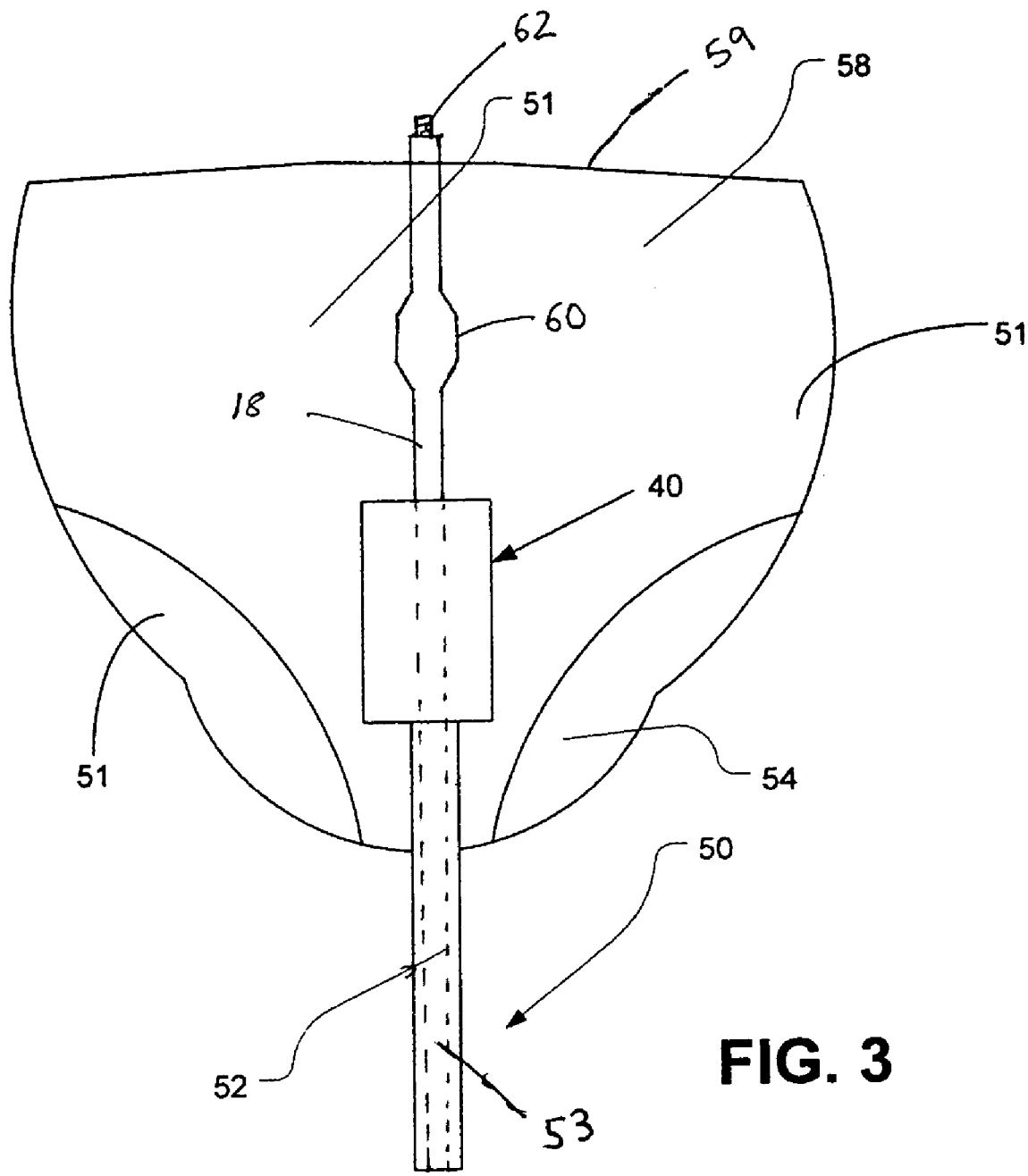
FIG. 3 is a schematic representation of an embodiment of a probe containing a transducer in accordance with the present invention.

FIG. 3 is a schematic representation of an embodiment of a probe 40 containing a transducer in accordance with the present invention. Probe 40 includes a catheter 52 having a distal end bearing an outer, reflector balloon 54; an inner, structural balloon 58; and a transducer subassembly 50 in accordance with the present invention. U.S. Pat. No. 6,635,054 and International Publication WO 2004/073505 disclose in more detail various probe structures of this type. The disclosures of U.S. Pat. No. 6,635,054 and International Publication WO 2004/073505 are incorporated herein, in their entirety, by reference. Supporting tube 18 communicates with the interior lumen 53 of catheter 52. Supporting tube 18 may also extend through the forward wall 59 of balloon 58. Alternatively, tube 18 may be connected to another tubular structure 60 which extends through forward wall 59 of balloon 58. Tube 18 may have a lumen to pass device such as a guide wire 62, or a sensor or pass a fluid such as a contrast medium. Because the tube 18 is continuous with the lumen 53 of catheter 52, and tube 18 or tubular structure 60 communicates with the forward wall 59, the device provides a continuous passage. The thermal insulation provided by sleeve 32 (FIG. 2) protects the devices or fluids introduced through tube 18 from the heat generated by the transducer.

Prior to use, probe 40 would be in a collapsed state, in which both balloons 54 and 58 are collapsed about transducer subassembly 50. Probe 40 could, for example, be for use in cardiac ablation, in which case it could be inserted over a guide wire, through a sheath which, in accordance with conventional practice, has previously been threaded through a patient's circulatory system and into the left atrium of the heart. However, there are other known techniques for positioning the probe, including surgical procedures.

Following that, structural balloon 58 may be inflated by injecting through a lumen of catheter 52 a liquid, such as saline solution, which has an ultrasonic impedance approximating that of blood. Reflector balloon 54 is inflated by injecting through another lumen of catheter 52 a gas, such as carbon dioxide. Owing to the different ultrasound impedance of the two inflation media, the interface between balloons 54 and 58 would then reflect ultrasound waves forward, through the distal portion of balloon 58.

Although a preferred embodiment of the invention has been disclosed for illustrative purposes, those skilled in the art will appreciate that many additions, modifications and substitutions are possible without departing from the scope and spirit of the invention.

The invention claimed is:

1. An ultrasonic transducer comprising:
   an active element having a front and a rear surface;
   a backing element in contact with the rear surface; and
   a support, the support being in contact with the backing element, wherein
   the backing element is hydrophobic, made of an insulating material which contains entrained air and is of sufficient thickness to provide substantial thermal insulation with respect to the active element.

2. The transducer of claim 1, wherein the active element is made of a piezoelectric material.

3. The transducer of claim 2, wherein the backing element is made of EPTFE.

4. The transducer of claim 3, wherein the active element is in the form of a sleeve, the front surface corresponding to the exterior surface of the sleeve and a rear surface corresponding to the interior surface of the sleeve, and the backing element is also in the form of a sleeve which is inward of the active element.

5. The transducer of claim 4, wherein at least one of the sleeves is substantially cylindrical.

6. The transducer of claim 5, wherein the backing element is a substantially cylindrical sleeve which contains a substantially cylindrical, axial bore, and the support is cylindrical and fits within the axial bore.

7. The transducer of claim 6, wherein the active element is between 0.5-16 millimeters long.

8. The transducer of claim 7, wherein the active element has an outside diameter between 1.5-2.5 millimeters.

9. The transducer of claim 8, wherein the backing element has a wall thickness between 0.25-1.25 millimeters.

10. In an ultrasonic transducer of the type including a hollow cylindrical active element made of a piezoelectric material and having inner and outer surfaces, the improvement comprising a backing element in contact with the inner surface and mounted on a cylindrical support, the backing element being made of an insulating material which contains entrained air and is hydrophobic.

11. The transducer of claim 10, wherein the insulating material EPTFE.

12. The transducer of claim 10, wherein the backing element is of sufficient thickness to provide substantial thermal insulation from the active element at a location inward of the backing element.

13. The transducer of claim 10, wherein the backing element is soft and does not significantly dampen the vibrations of the active element.

14. An ultrasonic transducer comprising:
    an active element having a front and a rear surface;
    a backing element in contact with the rear surface; and
    a support, the support being in contact with the backing element, wherein
    the backing element is made of a soft hydrophobic material containing entrained air that does not significantly dampen the vibrations of the active element.

15. The transducer of claim 14, wherein the active element is made of a piezoelectric material.

16. The transducer of claim 15, wherein the backing element is made of EPTFE.

17. The transducer of claim 16, wherein the active element is in the form of a sleeve, the front surface corresponding to the exterior surface of the sleeve and a rear surface corresponding to the interior surface of the sleeve, and the backing element is also in the form of a sleeve which is inward of the active element.

18. The transducer of claim 17, wherein at least one of the sleeves is substantially cylindrical.

19. The transducer of claim 18, wherein the backing element is a substantially cylindrical sleeve which contains a substantially cylindrical, axial bore, and the support is cylindrical and fits within the axial bore.

20. The transducer of claim 19, wherein the active element is between 0.5-16 millimeters long.

21. The transducer of claim 20, wherein the active element has an outside diameter between 1.5-2.5 millimeters.

22. The transducer of claim 21, wherein the backing element has a wall thickness between 0.25-1.25 millimeters.

* * * * *